United States Patent [19]
Kawaguchi et al.

[11] Patent Number: 5,476,656
[45] Date of Patent: Dec. 19, 1995

[54] SUBSTANCE BS-3

[75] Inventors: Katsumi Kawaguchi, Saitama; Eiichi Takahashi, Fukushima; Mitsuhiko Nishiki, Chiba; Satoshi Fujimoto; Toshiya Kase, both of Fukushima, all of Japan

[73] Assignee: Kureha Kagaku Kogyo Kabushiki Kaisha, Tokyo, Japan

[21] Appl. No.: 214,251

[22] Filed: Mar. 17, 1994

[30] Foreign Application Priority Data

| Mar. 18, 1993 | [JP] | Japan | 5-082511 |
| Apr. 6, 1993 | [JP] | Japan | 5-105177 |
| Jun. 15, 1993 | [JP] | Japan | 5-167357 |

[51] Int. Cl.$^6$ .............. A61K 35/00; C12P 13/06
[52] U.S. Cl. .............. 424/116; 435/101; 435/852
[58] Field of Search .............. 424/116; 435/101, 435/852

[56] References Cited

U.S. PATENT DOCUMENTS 4,975,371 12/1990 Kawaguchi ............ 435/101
5,215,919 6/1993 Miya et al. ............ 435/852
5,232,853 8/1993 Sugiyama et al. ............ 435/280
5,281,583 1/1994 Soma et al. ............ 514/83

OTHER PUBLICATIONS

Antioxidative Properties of Xanthan on the Autoxidation of Soybean Oil in Cyclodextrin Emulsion, Kazuko Shimada et al., J. Agric. Food Chem (1992) 40:945–948.

*Primary Examiner*—Herbert J. Lilling
*Attorney, Agent, or Firm*—Sughrue, Mion, Zinn, Macpeak & Seas

[57] ABSTRACT

Substance BS-3, a polysaccharide, produced by a microorganism belonging to the genus Klebsiella is disclosed, BS-3 having the following properties: main constituting sugar: rhamnose, galactose, glucose, and glucuronic acid; white to pale brown powder; easily soluble in water and sparingly soluble in methanol, ethyl acetate, benzene, etc.; viscosity: 1 to 8,000 cps; molecular weight: 1,000 to 10,000,000; positive in phenol-sulfuric acid reaction, carbazole-sulfuric acid reaction, Molisch's reaction, and ninhydrin reaction. BS-3 is useful as a heat-resistance stabilizer for a fat and oil emulsion and an anti-oxidant for fats and oils in an emulsion and also as an analgesic composition.

7 Claims, No Drawings

SUBSTANCE BS-3

FIELD OF THE INVENTION

This invention relates to a highly viscous polysaccharide produced by a microorganism belonging to the genus Klebsiella which is useful as a stabilizer for a heat-resistant oil-in-water (hereinafter abbreviated as O/W) emulsion and as a stabilizer for a water-rich water-in-oil (hereinafter abbreviated as W/O) emulsion, a process for producing the polysaccharide, a method for preventing oxidation of fats and oils in an emulsion by addition of the polysaccharide, and an analgesic composition containing the polysaccharide as an active ingredient.

A method for preventing fats and oils from oxidation is applicable to wide fields using fats and oils in an emulsified state, for example, foodstuffs, cosmetics, pharmaceuticals, agricultural chemicals, and industrial products such as coatings.

Background of the Invention

A number of polysaccharides produced by microorganisms are known. Typical examples of the polysaccharides include xanthan gum produced by *Xanthomonas campestris*, dextran produced by *Leuconostoc mesenteroides*, pullulan produced by *Aureobasidium pullulans*, and curdlan produced by *Alcaligenes faecalis*. These polysaccharides have found broad application as, for example, food additives, such as thickeners, dispersants, quality modifiers, emulsion stabilizers, etc. in the field of food; concrete fluidizing agents in the field of construction industry; and a plasma substitute in the medical field. Among known polysaccharides produced by microorganisms belonging to the genus Klebsiella is substance BS-1 produced by *Klebsiella pneumoniae* disclosed in U.S. Pat. No. 4,975,371 (corresponding to JP-B-2-19121, the term "JP-B" as used herein means an "examined published Japanese patent application").

Of these polysaccharides, xanthan gum and pullulan have high viscosity at room temperature and inhibit agglomeration of emulsion particles and are therefore widely utilized as an emulsion stabilizer. However, when they are exposed to high temperatures, the viscosity thereof is reduced, unavoidably causing emulsion break, i.e., phase separation into oil and water. Accordingly, they have difficulty in maintaining emulsion stability when they are added to foodstuffs subject to heat sterilization, such as retorted foods. In the field of emulsified fat and oil foodstuffs, it is known to use an emulsifying agent in combination with a stabilizer therefor, such as locust-bean gum, guar gum, xanthan gum, etc. However, the emulsion stability attained is still insufficient.

The market for fat spreads having a reduced fat and oil content and accordingly a lower calorie than margarine has been rapidly growing with the current pursuit of health. However, most of the products now on the market have a fat and oil content of 70% or more, lower than that of margarine only by about 10%. Those having a fat and oil content of 40% or less, i.e., a half of that of margarine have not yet been supplied in a great quantity because of economical and technical difficulties in preparing a W/O emulsion with an oil content of 40% or less. That is, lecithin or monoglyceride that is conventionally used emulsifier for margarine is not effective for forming a stable W/O emulsion in a low range of oil content. Polyglycerol polyricinoleate and a sucrose fatty acid polyester, though effective as an emulsifying agent, are not always applicable to fat spreads because they are not fit for the recent consumers' taste for high-grade foodstuffs.

Under these circumstances, there has been an increasing demand for an emulsion stabilizer which retains its emulsion stabilizing activity even in a high temperature and is effective even in a water-rich W/O emulsion.

On the other hand, fats and oils in foodstuffs undergo autoxidation to have a rancidity and an unusual taste. Saccharides, such as pentose, hexose and reducing disaccharides, have been reported to be powerful prooxidants in an O/W emulsion of linoleic acid, methyl linoleate, etc. Further, it is considered that a reducing sugar reduces a transition metal ion in an O/W emulsion and that the thus reduced metal ion accelerates oxidation of fats and oils.

To the contrary, sugar alcohols are known to be effective to prevent oxidation of safflower oil. Turning to polysaccharides, there are few reports on anti-oxidation action of polysaccharides though frequently used as an emulsion stabilizer for foodstuffs or cosmetics. The only report we find is that xanthan gum added as a stabilizer to an O/W emulsion of soybean oil containing tocopherol which was prepared in combination with β-cyclodextrin exhibited an anti-oxidation action (see Shimada et al., *J. Agric. Food Chem.*, vol. 40, pp. 945–948 (1992)). However, the emulsion that is stabilized by addition of xanthan gum lowers its viscosity when it is exposed to a high temperature to cause emulsion break as previously mentioned.

Known emulsifying agents to be used in foodstuffs or cosmetics include glycerol fatty acid esters, sucrose fatty acid esters, propylene glycol fatty acid esters, monoglyceride derivatives, lecithin, and saponin. It is only lecithin among them that is known to have an anti-oxidation action.

In brief, no substance showing both a heat-resistant emulsifying action and an anti-oxidation action has been developed. Hence, prevention of autoxidation of fats and oils in an emulsion has been achieved by using a combination of the above-mentioned emulsifying agent, an emulsion stabilizer (e.g., natural or synthetic high polymers or proteins), and an anti-oxidant (e.g., natural or synthetic anti-oxidants, such as ascorbic acid, tocopherol and polyphosphoric acid), etc.

On the other hand, a number of analgesic compositions based on various mechanisms of action have been proposed and put to practical use. Most of the available analgesic compositions are, however, chemically synthesized products. In other words, substances which are not taken in by human body in natural conditions have been utilized for relief of pain.

Polysaccharides known to have an analgesic activity include liposaccharides and hyaluronic acid. Liposaccharides have been reported to exhibit an analgesic action when they are given orally or injected intravenously (see *Bio Therapy*, vol. 6, p. 359 (1992)). However, liposaccharides are highly pyrogenic substances known as endotoxin, and use of such pyrogenic substances as analgesics gives rise to problems in practice. While hyaluronic acid has been put to practical use as a topical injection for joints, the analgesic action shown is believed to be ascribed to suppression of release of a paining substance or improvement of lubrication at joints through an action of covering the affected part. Accordingly, no effect is produced in oral administration.

Summary of the Invention

An object of the present invention is to provide a polysaccharide which is produced by culturing a specific microorganism and which, when used even in a relatively low concentration, exhibits a heat-resistant emulsifying action and stabilizes an emulsion, particularly a water-rich W/O emulsion, in a stable manner for a long time.

Another object of the present invention is to provide a method for preventing an emulsion of fats and oils from oxidation by using a polysaccharide having an excellent anti-oxidizing activity as well as an emulsion stabilizing activity.

A further object of the present invention is to provide an analgesic composition comprising a polysaccharide produced by a microorganism, which is effective in oral administration and has low toxicity. Considering that analgesic compositions are symptomatic, mild analgesic compositions with as low side effects as possible are desirable. In this sense, use of polysaccharides generally having low toxicity will be greatly advantageous in the medical field.

These and other objects of the present invention are accomplished by a substance, designated substance BS-3, obtained by culturing a substance BS-3-producing microorganism belonging to the genus Klebsiella, preferably a strain *Klebsiella terrigena* JCM 1687 (ATCC Deposit No. 55553), and recovering the active substance from the culture.

These and other objects of the present invention are also accomplished by a pharmaceutical analgesic composition containing, as an active ingredient, a polysaccharide having a molecular weight of from 10,000 to 10,000,000 which is obtained by culturing a microorganism belonging to the genus Klebsiella and recovering the active substance from the culture.

Detailed Description of the Invention

Substance BS-3 (hereinafter simply referred to as BS-3) according to the present invention is a polysaccharide produced by a BS-3-producing microorganism belonging to the genus Klebsiella and recovered from the culture of the BS-3-producing microorganism.

Physicochemical properties of BS-3 are as follows.
Appearance:
  white to pale brown powder;
(b) Solubility:
  easily soluble in water;
  sparingly soluble in methanol, ethyl acetate, chloroform or benzene;
  hydrolyzable with a mineral acid (e.g., hydrochloric acid, sulfuric acid) or an organic acid (e.g., acetic acid, trifluoroacetic acid);
(c) Viscosity:
  1 to 8000 cps (0.8% aqueous solution; 30° C.; shear rate: $1.96 \text{ s}^{-1}$);
(d) Main constituting sugar:
  rhamnose: 10.6–25.7%, galactose: 16.8–31.0%,
  glucose: 25.8–36.6%, glucuronic acid: 19.8–29.7%;
(e) Color reaction:
  phenol-sulfuric acid reaction: positive,
  carbazole-sulfuric acid reaction: positive,
  Molisch's reaction: positive,
  ninhydrin reaction: positive;
(f) Molecular weight:
  1,000 to 10,000,000;
(g) Elementary analysis:
  C: 30.0–40.0%, H: 4.0–6.0%, N: 0.0–1.0%;
(h) IR spectrum (KBr tablet; measured with Hitachi 260-50 produced by Hitachi, Ltd.):
  3400, 2930, 1610, 1410, 1310, 1160, 1070, 1040, 930, 890, 790, 600.

BS-3 can be produced by culturing a BS-3-producing microorganism belonging to the genus Klebsiella and recovering BS-3 from the culture. The BS-3-producing microorganism belonging to the genus Klebsiella typically includes *Klebsiella terrigena*, which is deposited under the name of *Klebsiella terrigena* JCM1687 strain in RIKEN (Institute of Physical and Chemical Research), Japan, and deposited under the number of ATCC 55553 (corresponding to original ATCC Deposit No. 33257) in American Type Culture Collection (ATCC), U.S.A.

As is well known, *Klebsiella terrigena* easily mutates on application of an appropriate mutation treatment, such as exposure to ultraviolet light, X-ray or radiation and a chemical treatment with a mutagenic compound (e.g., nitrsoguanidine, nitrogen mustard, acridine orange). All the thus obtained mutants should be construed as being included in strains of *Klebsiella terrigena* employable in the present invention as far as they are capable of producing BS-3.

BS-3 is produced by culturing the above-mentioned strain in a solid or liquid medium containing carbon sources, nitrogen sources and other nutrients necessary for growth under aerobic conditions, for example, by shake culture or aerating spinner culture. Examples of the carbon sources include sugars (e.g., lactose, sucrose, maltose, galactose, glucose, fructose); and glycerol. Among these, lactose are preferred. While not being limited as long as the strain may grow, the concentration of the carbon sources such as the sugars in the medium is generally from 1 to 10 w/v% as nitrogen, preferably from 3 to 7 w/v% as nitrogen. Examples of the nitrogen sources include organic substances (e.g., polypeptone, yeast extract, meat extract, tripticase peptone); and inorganic substances (e.g., nitrates, ammonium salts). While not being limited as long as the strain may grow, the concentration of the nitrogen sources in the medium is generally from 0.01 to 0.1 w/v%, preferably from 0.03 to 0.07 w/v%. From the standpoint of BS-3 productivity, organic nitrogen sources are preferred. If desired, the medium may further contain phosphates (e.g., potassium primary phosphate, potassium secondary phosphate); trace metals (e.g., iron, copper, magnesium, manganese, molybdenum, zinc, boron); vitamins (e.g., biotin, thiamine, vitamin $B_{12}$); and nucleic acids.

The culturing temperature is in the optimum growth range, i.e., generally from 20° to 37° C., preferably from 25° to 32° C. The pH of the medium is not particularly limited and usually from 3 to 11, and preferably in the vicinity of neutrality. With the progress of culturing, the viscosity of the culture broth increases with time, indicating production and accumulation of BS-3 in the culture. The culturing is theoretically conducted until the viscosity of the culture broth reaches the maximum. From the viewpoint of productivity, it is practical to continue culturing for 3 to 7 days.

After completion of the culturing, BS-3 produced and accumulated in the culture is recovered in a usual manner. In using a liquid medium, for example, the culture is diluted with water, and impurities including the microbial cells are removed by centrifugation (e.g., 39,800 g, 15 minutes), etc. Addition to the supernatant of a precipitating agent, such as an organic solvent (e.g., methanol, ethanol, isopropyl alcohol, acetone), a quaternary ammonium salt (e.g., cetyltrimethylammonium salt) or an acid amide (e.g., butylamide), causes BS-3 to precipitate. Among these, methanol is preferred for foodstuffs or pharmaceuticals, and isopropyl alcohol is preferred for industrial products. The precipitate is washed and dried to obtain BS-3 having the above-described properties.

If desired, the resulting BS-3 can be further purified to remove low-molecular weight portion thereof to obtain purified BS-3.

Purification of BS-3 can be carried out by repetition of dissolving the above-obtained BS-3 in water and precipitation using the above-mentioned precipitating agent. If necessary, the precipitates may be subjected to dialysis or chromatography for further purification.

The thus purified BS-3 according to the present invention has the following physicochemical properties.
(a) Appearance:
   odorless white powder;
(b) Solubility:
   easily soluble in water;
   sparingly soluble in methanol, ethyl acetate, chloroform or benzene;
   hydrolyzable with a mineral acid (e.g., hydrochloric acid, sulfuric acid) or an organic acid (e.g., acetic acid, trifluoroacetic acid);
(c) Viscosity:
   1 to 10,000 cps (0.8% aqueous solution; 30° C.; shear rate: $1.96\ s^{-1}$);
(d) Main constituting sugar:
   rhamnose: 10.6–25.7%, galactose: 16.8–31.0%,
   glucose: 25.8–36.6%, glucuronic acid: 19.8–29.7%;
(e) Color reaction:
   phenol-sulfuric acid reaction: positive,
   carbazole-sulfuric acid reaction: positive,
   Molisch's reaction: positive,
   ninhydrin reaction: negative;
(f) Molecular weight:
   10,000 to 10,000,000;
(g) Elementary analysis:
   C: 31.0–40.0%, H: 4.5–6.0%, N: 0.0–1.0%;
(h) IR spectrum (KBr tablet; measured with Hitachi 260-50 manufactured by Hitachi, Ltd.):
   3400, 2930, 2120, 1610, 1410, 1310, 1250, 1160, 1070, 1040, 930, 890, 840, 790, 600.

The method for preventing oxidation of fats and oils in an emulsion according to the present invention comprises adding the above-mentioned BS-3, preferably purified BS-3, to an emulsion of fats and oils. The emulsion to which the method of the present invention is suitably applied is an emulsion having a water to fats and oils ratio (hereinafter referred to a W/O ratio) of from 10:90 to 90:10, preferably from 40:60 to 90:10, by volume. BS-3 or purified BS-3 is generally added in a concentration of from 0.05 to 5% by weight, preferably from 0.1 to 3% by weight, in the form of either a powder or an aqueous solution. The resulting mixture is then homogenized by means of a general mixer or a homogenizer. There is thus provided an emulsion excellent in stability against viscosity variation and heat-resistant emulsion stability, in which fats or oils are effectively prevented from autoxidation.

Purified BS-3 according to the present invention has been found to exhibit an analgesic activity while having low toxicity and is therefore useful as an active ingredient of analgesics. BS-3 before being purified also exhibits an analgesic action and may be used as such as an active ingredient. The above-described purification of BS-3 is arbitrarily carried out if desired according to the dose form. In what follows, the term "BS-3" will be used to include not only "BS-3 before being purified" but also "purified BS-3".

When BS-3 is used as an analgesic composition, it may be used in any dose form convenient for obtaining the desired efficacy according to the kind and degree of a disease to be coped with. It may be used either alone or in combination with pharmaceutically acceptable adjuvants or other drugs. No adverse effects which seem to be side effects of BS-3 (e.g., death, abnormality when observed or dissected) were observed.

BS-3 can be administered either orally or non-orally and may be formulated into any dose form for oral and non-oral administration, such as powders, granules, tablets, capsules, suppositories, suspensions, solutions, ampules, and injectable solutions. These preparations may contain adjuvants, such as binders, vehicles, thickeners, wetting agents, disintegrators, and lubricants, according to the dose form.

BS-3 may be used in the form of pharmaceutical acceptable salts.

The present invention will now be illustrated in greater detail with reference to Examples, but it should be understood that the present invention is not construed as being limited thereto. All the percents and parts are by weight unless otherwise indicated.

EXAMPLE 1

Production of BS-3

A loopful by a platinum loop of *Klebsiella terrigena* JCM1687 having proliferated on a slant medium comprising 3% of lactose, 0.35% of tripticase peptone, 0.6% of potassium primary phosphate, 0.07% of magnesium sulfate, and 1.4% of agar was inoculated to 10 ml of a liquid medium having the same composition as described above except for containing no agar and pre-cultured at 28° C. for 1 day while shaking (180 rpm).

The whole microbial cells were aseptically inoculated to 100 ml of a liquid medium having the same composition as used in the preculturing and having been autoclaved at 120° C. for 15 minutes and incubated at 28° C. for 1 day while shaking (180 rpm). With the progress of culturing, the culture became viscous, revealing production and accumulation of BS-3.

The resulting culture broth was centrifuged at 39,800 g for 15 minutes to remove the microbial cells. To the supernatant was added double of the volume of ethanol to precipitate a pale brown solid, i.e., BS-3. The solid was collected by centrifugation and repeatedly washed with ethanol. The washed solid was redissolved in distilled water followed by lyophilization to obtain 0.95 g of a dry product.

The physicochemical properties of the dry product were examined, and the, results are shown below, from which the product was identified to be BS-3.
(a) Appearance:
   white to pale brown powder;
(b) Solubility:
   easily soluble in water;
   sparingly soluble in methanol, ethyl acetate, chloroform or benzene;
   hydrolyzable with a mineral acid;
(c) Viscosity:
   1 to 8000 cps (0.8% aqueous solution; 30° C.; shear rate: $1.96\ s^{-1}$);
(d) Main constituting sugar:
   rhamnose: 10.6–25.7%, galactose: 16.8–31.0%, glucose: 25.8–36.6%, glucuronic acid: 19.8–29.7%;
(e) Color reaction:
  phenol-sulfuric acid reaction: positive,
  carbazole-sulfuric acid reaction: positive,
  Molisch's reaction: positive,
  ninhydrin reaction: positive;
(f) Molecular weight:
  1,000 to 10,000,000;
(g) Elementary analysis:
  C: 30.0–40.0%, H: 4.0–6.0%, N: 0.0–1.0%;
(h) IR spectrum (KBr tablet; measured with Hitachi 260-50 produced by Hitachi, Ltd.):
  3400, 2930, 1610, 1410, 1310, 1160, 1070, 1040, 930, 890, 790, 600.

EXAMPLE 2

Purification of BS-3

In distilled water was dissolved 0.95 g of BS-3 prepared in Example 1, and the solution was centrifuged to remove any insoluble matter. Ethanol was added to the supernatant to reprecipitate a white solid (BS-3). The above redissolving in distilled water and reprecipitation with ethanol were repeated once more. The resulting precipitate was dissolved in distilled water, and the solution was dialyzed against pure water for 24 hours followed by lyophilization to obtain 0.60 g of purified product as a white mass.

The physicochemical properties of the purified product were examined, and the results obtained are shown below, from which the product was identified to be purified BS-3.
(a) Appearance:
  odorless white powder;
(b) Solubility:
  easily soluble in water;
  sparingly soluble in methanol, ethyl acetate, chloroform or benzene;
  hydrolyzable with a mineral acid;
(c) Viscosity:
  1 to 10,000 cps (0.8% aqueous solution; 30° C.; shear rate: 1.96 s$^{-1}$);
(d) Main constituting sugar:
  rhamnose: 10.6–25.7%, galactose: 16.8–31.0%,
  glucose: 25.8–36.6%, glucuronic acid: 19.8–29.7%;
(e) Color reaction:
  phenol-sulfuric acid reaction: positive,
  carbazole-sulfuric acid reaction: positive,
  Molisch's reaction: positive,
  ninhydrin reaction: negative;
(f) Molecular weight:
  10,000 to 10,000,000;
(g) Elementary analysis:
  C: 31.0–40.0%, H: 4.5–6.0%, N: 0.0–1.0%;
(h) IR spectrum (KBr tablet; measured with Hitachi 260-50 manufactured by Hitachi, Ltd.):
  3400, 2930, 2120, 1610, 1410, 1310, 1250, 1160, 1070, 1040, 930, 890, 840, 790, 600.

EXAMPLE 3

To 7.5 ml of a 2% aqueous solution of BS-3 obtained in Example 1 were added 16.5 ml of water and 6 ml of salad oil (Nisshin Salad Oil produced by THE NISSHIN OIL MILLS, LTD.). The mixture was heated to 60° C. and stirred in a homogenizer to prepare an emulsion having an oil-to-water volume ratio (hereinafter abbreviated as O/W ratio) of ¼. The resulting emulsion was an O/W type emulsion was heated to 60° C., 80° C., 100° C. or 120° C. for 20 minutes and then allowed to stand at room temperature. After 1 hour, 1 day, 4 days or 7 days, the emulsion was observed to obtain a volume percentage of the separated phase based on the total volume.

For comparison, the same heat stability test was carried out except for replacing BS-3 with the same amount of xanthan gum of reagent grade, commercially available sucrose monostearate, Tween 80, carboxymethyl cellulose (CMC) or substance BS-1 disclosed in U.S. Pat. No. 4,975,371 (corresponding to JP-B-2-19121).

The results obtained are shown in Tables 1 to 4 below.

TABLE 1

| Preservation After 60° C. Heat Treatment | | | | |
|---|---|---|---|---|
| Emulsion Stabilizer | 1 Hour | 1 Day | 4 Days | 7 Days |
| BS-3 | 0 | 2.6 | 5.3 | 5.3 |
| Xanthan gum | 2.6 | 55.3 | 94.3 | 97.4 |
| Sucrose monostearate (HLB 15) | 32.4 | 34.2 | 35.1 | 37.8 |
| Tween 80 | 5.6 | 39.5 | 44.1 | 50.0 |
| CMC | 7.7 | 7.7 | 7.9 | 7.9 |
| BS-1 | 0 | 5.3 | 39.5 | 39.5 |

TABLE 2

| Preservation After 80° C. Heat Treatment | | | | |
|---|---|---|---|---|
| Emulsion Stabilizer | 1 Hour | 1 Day | 4 Days | 7 Days |
| BS-3 | 2.6 | 2.6 | 5.3 | 36.8 |
| Xanthan gum | 60.5 | 60.5 | 97.3 | 97.3 |
| Sucrose monostearate (HLB 15) | 34.2 | 35.1 | 43.2 | 45.9 |
| Tween 80 | 37.8 | 40.5 | 47.4 | 50.0 |
| CMC | 18.4 | 18.4 | 21.1 | 21.1 |
| BS-1 | 5.3 | 5.3 | 36.8 | 39.5 |

TABLE 3

| Preservation After 100° C. Heat Treatment | | | | |
|---|---|---|---|---|
| Emulsion Stabilizer | 1 Hour | 1 Day | 4 Days | 7 Days |
| BS-3 | 2.7 | 5.3 | 8.1 | 36.8 |
| Xanthan gum | 65.8 | 65.8 | 97.4 | 100 |
| Sucrose monostearate (HLB 15) | 34.2 | 42.1 | 44.4 | 45.9 |
| Tween 80 | 36.8 | 42.1 | 47.4 | 50.0 |
| CMC | 100 | 100 | 100 | 100 |
| BS-1 | 5.3 | 5.3 | 39.5 | 39.5 |

TABLE 4

| Preservation After 120° C. Heat Treatment | | | | |
|---|---|---|---|---|
| Emulsion Stabilizer | 1 Hour | 1 Day | 4 Days | 7 Days |
| BS-3 | 5.4 | 10.8 | 36.8 | 40.5 |
| Xanthan gum | 75.7 | 75.7 | 97.4 | 100 |
| Sucrose monostearate (HLB 15) | 34.2 | 42.1 | 44.7 | 45.9 |
| Tween 80 | 36.8 | 43.6 | 81.6 | 100 |
| CMC | 100 | 100 | 100 | 100 |

TABLE 4-continued

| | Preservation After 120° C. Heat Treatment | | | |
|---|---|---|---|---|
| Emulsion Stabilizer | 1 Hour | 1 Day | 4 Days | 7 Days |
| BS-1 | 5.4 | 28.9 | 39.5 | 43.2 |

As is shown from Tables 1 to 4, BS-3 revealed the most excellent emulsion stabilizing activity in the heat treatment at a temperature of from 60° to 120° C.

EXAMPLE 4

0.15 g of BS-3 obtained in Example 1 was dissolved in a prescribed amount of distilled water at 60° C. in a homogenizer. To the homogenate were added 0.15 g of a polyglycerol fatty acid ester (HLB 15) and from 3 to 27 ml of salad oil (Nisshin Salad Oil produced by THE NISSHIN OIL MILLS, LTD.), followed by heating to 60° C. The mixture was homogenized while dropwise adding from 0 to 19.5 ml of distilled water kept at that temperature to prepare a W/O or O/W emulsion having a W/O ratio varying from 9/1 to 1/9 and containing 0.5% BS-3 and 0.5% polyglycerol fatty acid ester based on 30 ml of the total amount. For example, when an emulsion having a W/O ratio of 9/1 was prepared, the final amount of the salad oil and water may be adjusted to 27 ml and 3 ml, respectively. The emulsion was allowed to stand at room temperature, and the stability of the emulsion was observed after 1 hour and 1 day.

For comparison, the same stability test was carried out except for replacing BS-3 with the same amount of xanthan gum of reagent grade, commercially available locust-bean gum, guar gum or CMC.

The stability of the emulsion is represented as a volume percentage of a separated phase from the emulsion and it means that the lower the volume percentage of the separated phase is, the more excellent in stability the emulsion is. The type of the emulsion and the stability of the emulsion are shown in Table 5 below. All the emulsions having an W/O ratio of from 9/1 to 7/3 (not shown) were O/W type emulsions.

were excellent in stability, having a separated phase in a proportion of from 8.1 to 13.9%, the smallest of all the other emulsions.

EXAMPLE 5

Change of the anti-oxidation effect of BS-3 on fats and oils with time was examined as follows.

BS-3 prepared in the same manner as in Example 1 was added to a 20:80 (by volume) mixture of soybean oil and water at a concentration of 0.5%, and the mixture was homogenized to prepare an emulsion.

For comparison, β-cyclodextrin was added as an emulsifying agent to a 20:80 (by volume) mixture of soybean oil and water at a concentration of 1.5%, and to the mixture were further added 1 mM disodium ethylenediaminetetraacetate (hereinafter abbreviated as EDTA·2Na), 0.5% of soluble starch, and 0.5% of xanthan gum, followed by homogenization to prepare a comparative emulsion.

Each of the emulsions was preserved in an incubator kept at 37° C. for 50 days. The progress of oxidation was examined by determining changes in TBA value (colorimetric value obtained by a thiobarbituric acid reaction, indicative of a malondialdehyde content) and POV value (colorimetric value obtained by a potassium iodide method, indicative of a hydroperoxide content) with time. The results obtained are shown in Tables 6 and 7 below.

The emulsion stability was examined on each emulsion after being preserved at 37° C. for 7 days. Further, each emulsion was once heated to 80° C. and cooled to a room temperature, and the emulsion stability was observed immediately after the cooling. The emulsion stability is shown as volume of water separated from the 20:80 (by volume) mixture of oil and water. For example, when all water is separated, the emulsion stability indicates 80. The results obtained are shown in Table 8 below.

TABLE 5

| Emulsion | | 6/4 | | 5/5 | | 4/6 | | 3/7 | | 2/8 | | 1/9 | |
|---|---|---|---|---|---|---|---|---|---|---|---|---|---|
| Stabilizer | W/O Ratio: | 1 Hour | 1 Day | 1 Hour | 1 Day | 1 Hour | 1 Day | 1 Hour | 1 Day | 1 Hour | 1 Day | 1 Hour | 1 Day |
| BS-3 | Emulsion Type | W/O | | W/O | | W/O | | W/O | | W/O | | W/O | |
| | Stability* | 27 | 8.1 | 11.4 | 13.9 | 11.1 | 16.7 | emulsion break | | emulsion break | | emulsion break | |
| Xanthan gum | Emulsion Type | O/W | | O/W | | O/W | | W/O | | W/O | | W/O | |
| | Stability | | | | | | | 0 | 0 | emulsion break | | emulsion break | |
| Locust-bean | Emulsion Type | W/O | | W/O | | W/O | | W/O | | W/O | | W/O | |
| gum | Stability | 58.3 | 63.9 | 67.6 | 73.0 | 67.6 | 73.0 | 75.7 | 83.8 | 86.5 | 89.2 | emulsion break | |
| Guar gum | Emulsion Type | W/O | | W/O | | W/O | | W/O | | W/O | | W/O | |
| | Stability | 38.9 | 38.9 | 58.3 | 58.3 | 69.4 | 69.4 | 80.6 | 80.6 | 91.9 | 91.9 | emulsion break | |
| CMC | Emulsion Type | O/W | | O/W | | W/O | | W/O | | W/O | | W/O | |
| | Stability | | | | | 5.6 | 10.8 | 29.7 | 35.1 | emulsion break | | emulsion break | |

Note: *Percentage of the separated phase based on the total volume.

As can be seen from Table 5, in the water-rich emulsions having an W/O ratio of from 6/4 to 5/5, only those containing BS-3, locust-bean gum or guar gum were water-in-oil type emulsions. Above all, the emulsions containing BS-3

TABLE 6

Change of TBA Value (Absorbence at 532 nm) with Time

| Additive | 0 Day | 7 Days | 15 Days | 21 Days | 30 Days | 42 Days | 50 Days |
|---|---|---|---|---|---|---|---|
| BS-3 | 0.032 | 0.114 | 0.120 | 0.125 | 0.077 | 0.039 | 0.032 |
| Xanthan gum | 0.032 | 0.409 | 0.870 | 1.330 | 1.301 | 2.343 | 2.816 |
| Starch | 0.032 | 0.241 | 0.993 | 1.744 | 2.454 | 3.483 | 3.439 |
| EDTA.2Na | 0.032 | 0.085 | 0.396 | 0.706 | 1.398 | 2.625 | 3.056 |
| Control (no addition) | 0.032 | 0.759 | 1.596 | 2.432 | 2.871 | 3.768 | 4.452 |

TABLE 7

Change of POV Value (Absorbence at 353 nm) with Time

| Additive | 0 Day | 7 Days | 15 Days | 21 Days | 30 Days | 42 Days | 50 Days |
|---|---|---|---|---|---|---|---|
| BS-3 | 0.039 | 0.711 | 0.842 | 0.506 | 0.231 | 0.131 | 0.185 |
| Xanthan gum | 0.039 | 1.238 | 2.057 | 2.629 | 3.200 | 3.698 | 4.047 |
| Starch | 0.039 | 1.325 | 2.683 | 3.297 | 3.910 | 6.124 | 7.367 |
| EDTA.2Na | 0.039 | 0.475 | 1.369 | 1.797 | 2.480 | 4.186 | 5.288 |
| Control (no addition) | 0.039 | 2.082 | 2.921 | 3.551 | 4.495 | 6.718 | 11.207 |

TABLE 8

| | Emulsion Stability | |
|---|---|---|
| Additive | After Preservation (37° C., 7 days) | After Heating to 80° C. and Cooling to Room Temperature |
| BS-3 | 0 | 2.6 |
| Xanthan gum | 0 | 60.5 |
| Starch | 50 | 80 |
| EDTA.2Na | 47 | 80 |
| Control (no addition) | 70 | 80 |

As is apparent from Tables 6 and 7, progress of oxidation is significantly inhibited in the BS-3-added emulsion, revealing the marked effect of BS-3 addition. BS-3 exhibits an anti-oxidation activity incomparably superior to that of other polysaccharides, such as starch and xanthan gum.

Further, as shown in Table 8, the xanthan gum-added emulsion was as stable as the BS-3-added one when preserved at 37° C. for 7 days. However, the former lost its emulsion stability when heated at 80° C. for 20 minutes, whereas the latter was maintained in a stable state when similarly heat-treated.

Thus, BS-3 serves as not only an anti-oxidant for fats and oils in an emulsion but an emulsion stabilizer with heat resistance.

EXAMPLE 6

Anti-oxidation activity of BS-3 added in a concentration of 0.5% was compared with that of a commercially available anti-oxidant widely employed as a food additive added in a concentration of general use.

BS-3 prepared in the same manner as in Examples 1 was added to a 20:80 (by volume) mixture of soybean oil and water in a concentration of 0.5%, followed by homogenization to prepare an emulsion. For comparison, a commercially available anti-oxidant shown in Table 9 below was added to a 20:80 (by volume) mixture of soybean oil and water containing 1.5% of β-cyclodextrin as an emulsifying agent, followed by homogenization to prepare a comparative emulsion.

Each of the emulsions was preserved in an incubator kept at 37° C. for 14 days. The anti-oxidation effect on fats and oils was examined by determining TBA value and POV value on the 14th day. The results obtained are shown in Table 9.

TABLE 9

| Additive | Concentration of Additive (wt %) | TBA Value | POV Value |
|---|---|---|---|
| BS-3 | 0.5 | 0.035 | 0.591 |
| Sodium polyphosphate | 0.3 | 0.130 | 2.130 |
| EDTA.2Na | 0.02 | 0.100 | 1.520 |
| Butylhydroxytoluene | 0.02 | 0.061 | 1.038 |
| Ascorbic acid | 0.2 | 0.057 | 0.314 |
| Tocopherol | 0.02 | 0.176 | 2.723 |
| None (no addition) | — | 0.248 | 2.820 |

As can be seen from Table 9, BS-3 added in an amount of 0.5% has an anti-oxidation activity which is comparable to that of ascorbic acid added in a commonly employed amount and is greatly higher than that of the other commercially available anti-oxidants added in a commonly employed amount.

EXAMPLE 7

$LD_{50}$

Each of BS-3 and purified BS-3 solutions was once orally administered to a commercially available mouse (10 mice per group) by a probe. When 1,500 mg/kg per weight of the mouse which was a technical upper limit was administered, no mouse died. Accordingly, $LD_{50}$ of BS-3 or purified BS-3 is 1,500 mg/kg or more.

EXAMPLE 8

Analgesic Activity on PQ-induced Writhing

One part of purified BS-3 prepared in the same manner as in Example 2 was dissolved in 100 parts of water. The aqueous solution was orally administered to a commercially available mouse (3 mice per group). One control group received aspirin (acetylsalicylic acid), and another control group received physiological saline. After 1 hour from the administration, phenylquinone (PQ) was intraperitoneally administered to the animal at a dose of 2 mg/kg per weight of the mouse. The number of occurrence of PQ-induced writhing reactions (agony reactions) observed between 5 and 10 minutes from the PQ administration was recorded. The difference in total number of writhing reactions between the physiological saline group and that of the drug group was divided by the total number of writhing reactions of the physiological saline group to obtain a percent writhing inhibition. The test on purified BS-3 at a dose of 100 mg/kg was duplicated. The results obtained are shown in Table 10 below.

TABLE 10

| Test Group | Dose (mg/kg) | Writhing Inhibition (%) |
|---|---|---|
| Purified BS-3 | 100 | 60 |

TABLE 10-continued

| Test Group | Dose (mg/kg) | Writhing Inhibition (%) |
|---|---|---|
| Purified BS-3 | 100 | 69 |
| Purified BS-3 | 30 | 31 |
| Aspirin | 50 | 68 |

EXAMPLE 9

Analgesic Activity on Formalin-induced Hyperesthesia

The same purified BS-3 aqueous solution as used in Example 8 was orally administered to a commercially available mouse (3 mice per group). One control group received aspirin, and another control group received physiological saline. After 1 hour from the administration, 0.02 ml of a 1% formalin aqueous solution was injected to the sole of the right hind leg. The number of formalin-induced paw-licking reactions observed between 20 minutes and 30 minutes from the injection was recorded. The difference in total number of licking reactions between the physiological saline group and the drug group was divided by the total number of licking of the physiological saline group to obtain a percent paw-licking inhibition. The test on purified BS-3 at a dose of 100 mg/kg was duplicated. The results obtained are shown in Table 11 below.

TABLE 11

| Test Group | Dose (mg/kg) | Paw-Licking Inhibition (%) |
|---|---|---|
| Purified BS-3 | 100 | 58 |
| Purified BS-3 | 100 | 52 |
| Purified BS-3 | 30 | 6 |
| Aspirin | 50 | 60 |

It is seen that purified BS-3 at a dose of 100 mg/kg exhibits analgesic activity substantially equal to that of aspirin at a dose of 50 mg/kg.

As having been demonstrated in the foregoing Examples, BS-3 and purified BS-3 according to the present invention can be supplied stably and are useful as an emulsion stabilizer.

Since an emulsion containing BS-3 is thermally stable, BS-3 is applicable as an emulsion stabilizer for foodstuffs subject to sterilization by heating.

By addition of BS-3, even a water-rich system can be emulsified to prepare a stable water-in-oil emulsion. Therefore, BS-3 makes it feasible to prepare a creamy fat spread of satisfactory taste, though having low calories.

Further, addition of BS-3 to an emulsion system of fats and oils provides an emulsion system in which the fats and oils are effectively prevented from oxidation, while the system exhibiting excellent viscosity stability and heat resistance.

According to the process of the present invention, such useful BS-3 can be produced with ease by culturing of a microorganism. BS-3 according to the present invention is highly safe, consistent with the environment, and capable of providing an emulsion insusceptible to oxidation.

Since purified BS-3 of the present invention has low toxicity as having an $LD_{50}$ of 1,500 mg/kg or more, the analgesic according to the present invention containing BS-3 as an active ingredient has high safety and produces an analgesic effect even when administered orally.

While the invention has been described in detail and with reference to specific examples thereof, it will be apparent to one skilled in the art that various changes and modifications can be made therein without departing from the spirit and scope thereof.

What is claimed is:

1. Substance BS-3 produced by a microorganism belonging to the genus Klebsiella, wherein the substance BS-3 has the following physicochemical properties:
  (a) Appearance:
    white to pale brown powder;
  (b) Solubility:
    easily soluble in water;
    sparingly soluble in methanol, ethyl acetate, chloroform or benzene;
    hydrolyzable with a mineral acid;
  (c) Viscosity:
    1 to 8,000 cps (0.8% aqueous solution; 30° C.; shear rate: 1.96 $s^{-1}$);
  (d) Main constituting sugar:
    rhamnose: 10.6–25.7%, galactose: 16.8–31.0%, glucose: 25.8–36.6%, glucuronic acid: 19.8–29.7%;
  (e) Color reaction:
    phenol-sulfuric acid reaction: positive,
    carbazole-sulfuric acid reaction: positive,
    Molisch's reaction: positive,
    ninhydrin reaction: positive;
  (f) Molecular weight:
    1,000 to 10,000,000;
  (g) Elemental analysis:
    C: 30.0–40.0%, H: 4.0–6.0%, N: 0.0–1.0%;
  (h) IR spectrum (KBr tablet):
    3400, 2930, 1610, 1410, 1310, 1160, 1070, 1040, 930, 890, 790, 600.

2. The substance BS-3 as claimed in claim 1, wherein the substance BS-3 is a purified substance BS-3 having the following physicochemical properties:
  (a) Appearance:
    odorless white powder;
  (b) Solubility:
    easily soluble in water;
    sparingly soluble in methanol, ethyl acetate, chloroform or benzene;
    hydrolyzable with a mineral acid;
  (c) Viscosity:
    1 to 10,000 cps (0.8% aqueous solution; 30° C.; shear rate: 1.96 $s^{-1}$);
  (d) Main constituting sugar:
    rhamnose: 10.6–25.7%, galactose: 16.8–31.0%, glucose: 25.8–36.6%, glucuronic acid: 19.8–29.7%;
  (e) Color reaction:
    phenol-sulfuric acid reaction: positive,
    carbazole-sulfuric acid reaction: positive,
    Molisch's reaction: positive,
    ninhydrin reaction: negative;
  (f) Molecular weight:
    10,000 to 10,000,000;
  (g) Elemental analysis:
    C: 31.0–40.0%, H: 4.5–6.0%, N: 0.0–1.0%;

(h) IR spectrum (KBr tablet):
3400, 2930, 2120, 1610, 1410, 1310, 1250, 1160, 1070, 1040, 930, 890, 790, 600.

3. The substance BS-3 as claimed in claim 1, wherein the microorganism is a strain *Klebsiella terrigena* JCM1687 (ATCC Deposit No. 55553) or a mutant thereof.

4. A process for producing the substance BS-3 as claimed in claim 1, comprising culturing a BS-3-producing microorganism belonging to the genus Klebsiella and recovering the substance BS-3 from the culture.

5. A pharmaceutical composition comprising an active ingredient together with a pharmaceutically acceptable carrier, wherein the active ingredient is the substance BS-3 of claim 1 having a molecular weight of from 10,000 to 10,000,000 which is produced by a microorganism belonging to the genus Klebsiella.

6. The pharmaceutical composition as claimed in claim 5, wherein the microorganism is a strain *Klebsiella terrigena* JCM1687 (ATCC Deposit No. 55553) or a mutant thereof.

7. A pharmaceutical composition comprising an active ingredient together with a pharmaceutically acceptable carrier, wherein the active ingredient is a polysaccharide produced by a microorganism belonging to the genus Klebsiella having the following physiochemical properties:

(a) Appearance:
  odorless white powder;

(b) Solubility:
  easily soluble in water;
  sparingly soluble in methanol, ethyl acetate, chloroform or benzene;
  hydrolyzable with a mineral acid;

(c) Viscosity:
  1 to 10,000 cps (0.8% aqueous solution; 30° C.; shear rate: $1.96 \, s^{-1}$);

(d) Main constituting sugar:
  rhamnose: 10.6–25.7%, galactose: 16.8–31.0%, glucose: 25.8–36.6%, glucuronic acid: 19.8–29.7%;

(e) Color reaction:
  phenol-sulfuric acid reaction: positive, carbazole-sulfuric acid reaction: positive, Molisch's reaction: positive, ninhydrin reaction: negative;

(f) Molecular weight:
  10,000 to 10,000,000;

(g) Elemental analysis:
  C: 31.0–40.0%, H: 4.5–6.0%, N: 0.0–1.0%;

(h) IR spectrum (KBr tablet):
  3400, 2930, 2120, 1610, 1410, 1310, 1250, 1160, 1070, 1040, 930, 890, 840, 790, 600.

\* \* \* \* \*